United States Patent
Csanyi et al.

(10) Patent No.: US 8,843,509 B2
(45) Date of Patent: Sep. 23, 2014

(54) METHOD AND SYSTEM FOR ESTIMATING PROPERTIES OF ATOMS AND MOLECULES

(75) Inventors: Gabor Csanyi, Cambridge (GB); Albert Bartok-Partay, Cambridge (GB); Imre Kondor, Pasadena, CA (US)

(73) Assignee: Cambridge Enterprise Limited, New York, NY (US)

( * ) Notice: Subject to any disclaimer, the term of this patent is extended or adjusted under 35 U.S.C. 154(b) by 502 days.

(21) Appl. No.: 12/996,530

(22) PCT Filed: Jun. 5, 2009

(86) PCT No.: PCT/GB2009/001414
§ 371 (c)(1),
(2), (4) Date: Mar. 14, 2011

(87) PCT Pub. No.: WO2009/147408
PCT Pub. Date: Dec. 10, 2009

(65) Prior Publication Data
US 2011/0161361 A1 Jun. 30, 2011

(30) Foreign Application Priority Data
Jun. 6, 2008 (GB) .................................. 0810413.5

(51) Int. Cl.
*G06F 17/30* (2006.01)
*G06F 19/00* (2011.01)

(52) U.S. Cl.
CPC .................................... *G06F 19/704* (2013.01)
USPC ....................................................... 707/769

(58) Field of Classification Search
USPC ....................................................... 707/769
See application file for complete search history.

(56) References Cited

U.S. PATENT DOCUMENTS

| | | | | |
|---|---|---|---|---|
| 6,106,562 A | * | 8/2000 | Teter et al. | 703/12 |
| 8,165,818 B2 | * | 4/2012 | Nicholls | 702/19 |
| 2002/0062155 A1 | | 5/2002 | Itai et al. | |
| 2003/0167135 A1 | | 9/2003 | Ewing | |
| 2003/0224338 A1 | * | 12/2003 | Emberly et al. | 434/281 |
| 2003/0229456 A1 | * | 12/2003 | Beger et al. | 702/27 |
| 2004/0103080 A1 | * | 5/2004 | Samukawa | 707/1 |
| 2004/0137432 A1 | * | 7/2004 | Itai et al. | 435/6 |
| 2005/0144147 A1 | * | 6/2005 | Lee et al. | 706/12 |
| 2005/0278124 A1 | * | 12/2005 | Duffy et al. | 702/19 |
| 2006/0195267 A1 | | 8/2006 | Nicholls | |

FOREIGN PATENT DOCUMENTS

EP    0 431 189 A1    6/1990

OTHER PUBLICATIONS

Castillo et al., ("The hydrogen atom via the four-dimensional spherical harmonics"), Oct. 2007, Revista Mexicana De Fisica 53, pp. 407-414.*
Kondor, Risi, "A Novel Set of Rotationally and Translationally Invariant Features for Images Based on the Non-commutative Bispectrum", arxiv cs/0701127v3, Dec. 28, 2007, 9 pages.

(Continued)

*Primary Examiner* — Alex Gofman
*Assistant Examiner* — Michael Le
(74) *Attorney, Agent, or Firm* — Hickman Palermo Truong Becker Bingham Wong LLP (57) ABSTRACT

A method and system for modelling atomic or molecular level structures, or the atomic or molecular energies or forces in such structures. The method and system use a Gaussian Process to estimate properties at the atom or molecular level in such structures.

23 Claims, 2 Drawing Sheets

(56) References Cited

OTHER PUBLICATIONS

Varshalovich, D.A., "Wigner D-Functions", Chapter 4, Quantum Theory of Angular Momentum, published in the United States, World Scientific Pub Co Inc., Oct. 1998, 59 pages.

Varhalovich, D.A. et al., "Clebsch-Gotdan Coefficients and 3jm Symbols", Quantum Theory of Angular Momentum, Chapter 8, published in United States, World Scientific Pub Co Inc, Oct. 1988, 55 pages.

MacKay, D., "Information Theory, Inference, and Learning Algorithms," Chapter 45, 15 pages, published in United Kingdom, 2003.

Chen, William, "Lessons From the Design of a Novel Atomic Potential for Protein Folding", Published by Cold Spring Harbor Laboratory Press, 2005, 12 pages.

Obrezanova, Olga et al., "Gaussian Processes: A Method for Automatic OSAR Modeling of ADME Properties", American Chemical Society, 2007, 12 pages.

Rasmussen, Carl, "Advances in Gaussian Process", Tutorial at NIPS 2006 in Vancouver, Canada, Dec. 4, 2006, 56 pages.

Meremianin, A.V. "Multipole Expansions in Four-Dimensional Hyperspherical Harmonics", Institute of Physics Publishing, Journal of Physics A: Mathematical and General, published in United Kingdom, Mar. 8, 2006, 15 pages.

Quinonero-Candela et al., "A Unifying View of Sparse Approximate Gaussian Process Regression", Journal of Machine Learning Research 6, Dec. 2005, 21 pages.

Ahnert et al., "Implementations of Information Theory in Molecular Dynamics, Quantum Measurement and Genetic Data Analysis", University of Cambridge, Aug. 2005, 162 pages.

Skilling, John, "Nesting Sampling for General Bayesian", International Society for Bayesian Analysis, 2006, 28 pages.

Snelson et al., "Sparse Gaussian Processes Using Pseudo-inputs", Gatsby Computational Neuroscience, 18 Advances in Neural Information Processing Systems 18, published in United Kingdom, 2006 Unit, 8 pages.

European Patent Office, "International Search Report with Written Opinion", in Application No. PCT/GB2009/001414, Applicant: Cambridge Enterprise Limited, Dated Dec. 28, 2009, 21 pages.

\* cited by examiner

METHOD AND SYSTEM FOR ESTIMATING PROPERTIES OF ATOMS AND MOLECULES

The present invention relates to the general field of modelling atomic motion or atomic-level structures, and in particular although not exclusively to a computer system that enables simulation of atomic structure and motion in molecules or solids. It finds application to a wide range of manufacturing industries including pharmaceutical and other life sciences as well as biotechnology, aerospace, automotive, materials engineering, chemical engineering and chemistry, nanotechnology and electronics.

BACKGROUND

Companies in the above fields who want to understand the fundamental material mechanisms that underlie the operation of their technology or their manufacturing process, or who want to improve the performance of the same, often turn to modelling material processes on the atomic scale. This is done by using a computer running a software that simulates the motion of atoms or molecules given appropriate initial or boundary conditions.

Computer simulation of atomic motion involves approximating the Schrödinger equation, which is the real underlying equation that describes the behaviour of matter. Approximations are necessary because solving it directly for more than a few particles is currently impossible and likely to remain so for the foreseeable future. There is a large hierarchy of approximations that are widely employed, ranging from the very accurate and slow Quantum Chemistry methods to the very fast but inaccurate empirical interatomic potentials (also known as "force fields"). In practice, there is a gap in this series of models. All presently used quantum mechanical models, involve solving the equations that describe the electrons in order to arrive at the potential energy of the atoms, are many orders of magnitude slower than any interatomic potential model. Correspondingly, the accuracy of quantum mechanical models can be improved substantially and systematically (at correspondingly increased computational cost), while even the best interatomic potentials have serious and inherent shortcomings.

In practice, even the fastest (and not very accurate) quantum mechanical model can only simulate about 1000 atoms for a few tens of picoseconds on the type of parallel computer cluster that is generally available to industry and academia. The typical interatomic potentials that are capable of handling millions of atoms are not able to describe the all-important bond breaking and bond forming processes that underlie atomistic processes, while even the best and most costly interatomic potentials have only been shown to be able to do this in very niche situations.

Embodiments of this invention aim to address this problem and allow an approximation method and system that is fast by comparison to quantum chemistry and accurate by comparison to known force field techniques.

Aspects of the invention are defined in independent claims 1, 17 and 19.

Embodiments of the invention bridge the above gap in speed and accuracy. It postulates the existence of locally determined information, e.g. the energy of an atom, or other properties such as force which, for a given atom, can be calculated by just considering the close neighbourhood of the atom. These properties are then used to approximate the total energy of the atomic system, or to derive the motion of the atoms therefrom. Without assuming any fixed functional form, a database of atomic neighbourhoods and corresponding property values is built by solving or approximating a solution to a quatum mechanical model, as described above. This is a one-time cost, so the embodiments do not need to solve the electronic problem directly henceforth, and thus the speed of some embodiments will be similar to that of other interatomic potentials. On the other hand, because embodiments may approximate the potential energy function of any desired quantum mechanical model, accuracy of some embodiments is close to that of the latter. In embodiments, the formulation allows for a systematic improvement of the approximation and hence the accuracy, by enlarging the database. In some embodiments, the systematic improvement can even be done "on the fly", because the method may provide an estimate of its own error, so new database entries can be generated in situations where the approximation is predicted to be not good enough.

The invention is now described with reference to the accompanying drawings in which.

Figure 1:
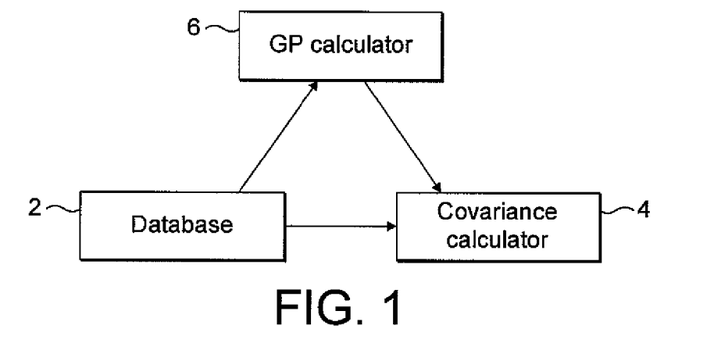
FIG. 1 shows an embodiment schematically as a block diagram.

In overview, an embodiment comprises the following components:
1. A Database 2 of atomic neighbourhoods and respective property values for an atom in the neighbourhood
2. A Covariance calculator 4 which calculates a covariance function from the database
3. A Gaussian Process calculator 6 which estimates a value of parameter such as energy for an atom in a new neighbourhood.

Gaussian Process

A Gaussian Process (GP) is used to infer the potential energy values from the database. The GP is a standard, albeit recently popularised technique in computer science and machine learning. Rather than working with a predefined functional forms with free parameters, it postulates a probability distribution on the entire space of possible functions (the so-called prior distribution, denoted P(T), where T represent possible "Theories"), then takes the database as evidence (observed data, D) to deduce at an improved probability distribution (the posterior distribution, P(T|D)) using Bayes' Theorem:

$$P(T \mid D) = \frac{P(D \mid T)P(T)}{P(D)}$$

The likelihood, P(D|T) represents the degree to which a given piece of data D is likely to have been observed, if the theory T were true. The power of this theorem lies in the fact that prior beliefs can be encoded in the prior distribution P(T). In the present case, this is information about smoothness of the target function. This greatly reduces the amount of data that is required, and prevents overfitting. The specification of a Gaussian Process starts with the Covariance Function, C(x, x'), which will be detailed below. Here it will suffice to state that C is a similarity measure: it takes two points x and x' from the input space and compares them, returning 1 if they are identical and 0 if they are completely unrelated.

Let us denote the available data D by {Y, X}, where the X={$x^{(n)}$} is a set of N vectors describing the atomic neighbourhood configurations of N central atoms (e.g. the list of cartesian coordinates of all neighbours of the atom within some cutoff distance e.g. 3 Å, relative to the central atom) and $Y=\{Y^{(n)}\}$ is the corresponding set of calculated property values, e.g. energies of the respective central atoms. The Gaussian Process will yield a probability for models $y(x)$ which predict the property, e.g. the energy. $y(x)$ corresponds to the possible theories, T above.

Bayes' Theorem is thus $$P(y(x)|Y,X) \propto P(Y|y(x),X)P(y(x))$$

The prior distribution $P(y(x))$ is taken to be a multivariate normal distribution with zero mean and covariance C, $$P(y(x^{(1)}), \ldots, y(x^{(n)})) = N(O,C),$$

where the matrix C has elements $C(x^{(n)}, x^{(n')})$. The above prior is equivalent to the assumption that properties of configurations that are similar are correlated, whereas properties of configurations that are not similar are uncorrelated. The central result we use is that the posterior distribution for the property at a new point $y(x')$ is also a multivariate normal distribution, $$P(y(x')|Y,X) = \mathcal{N}(\langle y' \rangle, \sigma_{y'}^2),$$

with mean and variance $$\langle y' \rangle = k^T C^{-1} Y$$

$$\sigma_{y'}^2 = \kappa - k^T C^{-1} k$$

where the vector k has components $k_n = C(x', x^{(n)})$ and describes the similarity of the new point to the ones in the for which data is known, and $\kappa = C(x', x')$. Although the output of Bayes' Theorem is an entire distribution over the range of potential functions, in practice, the above mean of the posterior distribution is customarily adopted as an estimate of the potential energy, and the variance of the posterior forms an indication of the error. This variance, evaluated for a new atomic configuration, gives an indication of how different this configuration is from the ones already in the database, and therefore how large the error is likely to be. For a detailed discussion of the Gaussian Process, see the books by Rasmussen or MacKay, referenced below and herewith incorporated herein by reference.

Similarity Measure

We now describe the similarity measure or covariance function, which is the key element in using the Gaussian Process, and is used to define the covariance of the above multivariate probability distributions. Given two instances of atomic configurations (either both observed data, or one observation and one new configuration for which an estimate is needed), the covariance function captures how similar they are. This covariance function must thus respect basic physical symmetries of the system, e.g. if two neighbourhood configurations are related by just a global rotation in space, a global translation of coordinates, or just by the relabelling of the same type of atoms, they are not physically different. On the other hand, the covariance function must detect and measure correctly all other differences in the two configurations. The covariance function is a "distance measure" in the space of neighbourhoods.

The list of Cartesian coordinates of neighbours x cannot be used directly, because they are not invariant with respect to neither rotations, nor permutations. An example of a covariance function, which does satisfy the above requirements is as follows. We want to describe and compare the neighbourhood configurations of atoms. Let us take the position of the atom whose neighbourhood we want to specify as the origin of our coordinates in space. We start by constructing an atomic density function from relative positions with respect to the central atom, $r_i$, of the neighbouring atoms:

$$\rho(r) = \sum_i \delta(r - r_i)$$

where $\delta$ is the Dirac delta function and r is a relative position relating to the central atom. This density is invariant to permutations and global translations. We express the atomic density function in a spherical harmonic basis:

$$\rho(r) = \sum_{n=0}^{\infty} \sum_{l=0}^{\infty} \sum_{m=-l}^{l} c_{l,n}^m b_n(r) Y_l^m(\theta, \phi)$$

where $Y_l^m$ denotes the spherical harmonics, and $b_n^{(r)}$ are a set of radial basis functions. e.g. Gaussians, $b_n^{(r)} = \exp[-((r-r_n)/\sigma)^2]$, where $r_n$ are uniformly spaced around the mean atomic bond length (e.g. 2.35 Å in silicon) and $\sigma = 0.45$ Å, for example. We need to obtain rotationally invariant combinations of the coefficients $c_{l,n}^m$. Such combinations are provided by the bispectrum.

The bispectrum is a representation in signalling theory, with prior usage in the literature with Cartesian coordinates, in which case it is invariant with respect to time-shifting or spatial translation of the signal. To understand what the bispectrum is in this case, consider how the $c_{l,n}^m$ themselves transform under rotation. For the purpose of this discussion, we drop the n index, and denote the set of coefficients $c_l^m$ by the vector $c_l$. Under a rotation by angle $\alpha$ around an axis a, we have $c_l \rightarrow D_l c_l$, where $D(a, \alpha)$ denotes the Wigner D-matrix, which are irreducible representations of the three dimensional rotation group SO(3). Thus if we form the scalar product $p_l = c_l^\dagger c_l$, it will be invariant under rotations, because the D-matrices are unitary, $D^\dagger D = I$. However, the set of $p_l$ values form a very poor representation, they are insensitive to the relative rotations within each l channel. To solve this problem, we consider how the tensor product of two $c_l$ vectors transforms: $c_{l1} \otimes c_{l2} \rightarrow (D_{l1} \otimes D_{l2}) c_{l1} \otimes c_{l2}$. We need to use a theorem from representation theory, which states that for simple Lie groups (which includes the rotation group that we are concerned with here), every representation can be written as a direct sum of irreducible representations, $$D_{l_1} \otimes D_{l_2} = C_{l_1,l_2}^\dagger \left[ \bigoplus_{l=|l_1-l_2|}^{l_1+l_2} D_l \right] C_{l_1,l_2}$$

where the $C_{l1,l2}$ are the Clebsch-Gordan coefficients.

We express this matrix as a direct sum of smaller matrices $g_l$, each transforming according to a different Wigner-matrix:

$$C_{l_1 l_2} c_{l_1} \otimes c_{l_2} = \bigoplus_{l=|l_1-l_2|}^{l_1+l_2} g_{l,l_1,l_2}$$

The transformation of this object is as follows:

$$C_{l_1 l_2} c_{l_1} \otimes c_{l_2} \rightarrow \left[ \bigoplus_{l=|l_1-l_2|}^{l_1+l_2} D_l \right] C_{l_1 l_2} c_{l_1} \oplus c_{l_2} = \bigoplus_{l=|l_1-l_2|}^{l_1+l_2} D_l g_{l,l_1,l_2}$$

Therefore the g matrices transform according to $$g_{l,l_1,l_2} \rightarrow D_l g_{l,l_1,l_2}$$

We are finally able to write down the new invariants, which are $$p_{l,l_1,l_2} = c_l^\dagger g_{l,l_1,l_2}$$

Or, reintroducing the n indices:

$$p_{l,l_1,l_2}^{n,n_1,n_2} = c_l^{n\dagger} g_{l,l_1,l_2}^{n,n_1,n_2}$$

And in more detail:

$$p_{l_1,l_2,l}^{n,n_1,n_2} = \sum_{m_1=-l_1}^{l_1} \sum_{m=-l}^{l} (c_l^{n,m})^* C_{l,l_1,l_2}^{m,m_1,m-m_1} c_{l_1}^{n_1,m_1} c_{l_2}^{n_2,m-m_1}$$

These p values constitute the bispectrum of the original density $\rho_{(r)}$. This is a vastly redundant set, and it is enough, e.g. to take $l, l_1, l_2$ values from bispectra belonging to neighbouring radial basis functions (e.g. $n_1 = n+1$, $n_2 = n+2$, remembering that the full array of invariants includes radial indices n, $n_1$, $n_2$ as well), e.g. $p_k = c_{l,n}^\dagger g_{l,l_1,l_2}^{n,n+1,n+2}$, where k corresponds to an index over all selected p values, e.g. over all settings of l, $l_1$, $l_2$ and n.

Denoting the set of selected bispectral invariants by $p_k(x)$, the covariance function for two configurations x and x' is written as $$C(x, x') = e^{-\sum_k \left[\frac{p_k(x) - p_k(x')}{\sigma_k}\right]^2}$$

The free parameters $\sigma_k$ represent scale variables which need to be optimised to get the best similarity measure appropriate to the system at hand. One way to optimise them is to use maximise the log-likelihood function log P(Y, X|T)=$-\frac{1}{2}\frac{1}{2}$ log det© $-\frac{1}{2}\frac{1}{2}Y^T C^{-1} Y$ by searching the space of possible $\sigma_k$ values using the recently introduced Nested Sampling method (see Skilling referenced below, herewith incorporated herein by reference). Note that the Gaussian form of this covariance function has nothing to do with the "Gaussian" in the "Gaussian Process", the latter refers to the Gaussian nature of the multivariate normal distributions described above.

One problem of the transformation described above is the separation of the density into the product of a radial and an angular function. This introduces the necessity of choosing radial functions, and also increases the number of parameters, because for each radial function (i.e. each n), there will be a complete angular bispectrum (l, $l_1$, $l_2$), so the number of dimensions of our invariants is very large. The alternative embodiment discussed below reduces this by projecting the entire object density p(r) into the surface of the 4D sphere and then expanding it in hyperspherical harmonics, which has a single set of angular bispectral invariants, just indexed by l, $l_1$, $l_2$. in the calculation of the invariants.

In an alternative embodiment, a different, although related, transformation is used. In this embodiment the atomic density (or, equivalently in the above model, the atomic coordinates), which is a 3D scalar field, is projected onto the surface of a four-dimensional sphere. The resulting density/coordinates are then expanded, analogously to the transformation described above, in (hyper) spherical harmonic functions. The bispectrum invariants are then formed from the hyperspherical harmonic functions. The new invariants $p_{l,l1,l2}$ are invariant under rotations of the 4D sphere, including rotations and translations of the 3D sphere. The details of the calculation of $p_l$, $l_1$, $l_2$, in this embodiment are described in APPENDIX I below (where $U_l^{mm'}$ is the 4D analogue of $Y_l^m$).

By projecting the coordinates onto a 4D sphere, the spherical harmonics can be calculated directly without the need for the radial basis function $b_n$ and the associated free parameters and additional indices in the set of invariants. Accordingly, the full set of $p_l$, $l_1$, $l_2$ can be used for the set $p_k$ in the calculation of the covariance function C(x, x').

Details of the implementation of the above calculations will be apparent to the person skilled in the art and can be found in the Varshalovich et al and Meremianin references cited below and herewith incorporated by reference herein.

In the above exposition, we assumed for the sake of simplicity that our atomic system contains one kind of atom only, e.g. silicon. But the method can be readily extended to heteroatomic environments. In this case, each database entry for an atomic neighbourhood configuration would also contain the atomic type of the central atom and that of each neighbour. In the construction of the invariants, we form a separate atomic density function $\rho_z$ for each atomic number Z, and the invariants $p_k$ mix together spherical harmonic coefficients from densities belonging to difference atomic numbers, e.g. $p = c_{l,n}^\dagger g_{l,l1,l2}^{n,n+1,n+2,Z1,Z2,Z3}$. Alternatively, each atomic type could be represented by a multiplicative factor $\alpha_Z$ in the construction of the atomic density above, in which case no change is necessary to the rest of the bispectral invariant construction.

Database

A number of atomic neighbourhood configurations are stored in the database, each referring to a central atom, together with the associated property values, e.g. the energy of the central atom, or other properties necessary for computing the total energy of the system. It is not necessary to store the original coordinates of the neighbour atoms (denoted by combined symbol x above), it is enough to store for each configuration, the set of invariants $p_k(x)$, together with the associated property we want to predict, y(x).

This database is interrogated every time an estimate is required for a new configuration, and a prediction is produced, together with an error estimate.

Figure 2:
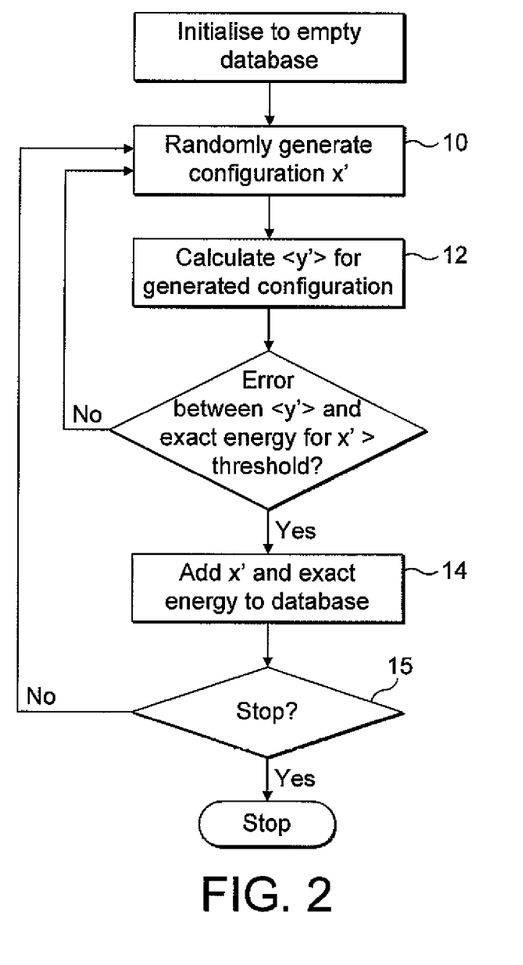
FIG. 2 shows a corresponding flow diagram for initially building a database of the embodiment.

The building of the database is as follows with reference to FIG. 2. We start with an empty database, which, by construction, will predict zero energy for all configurations. Then atomic neighbourhood configurations with low to moderate potential energies are generated randomly at step 10, an energy (or other property)<$y^1$> is predicted for each configuration at step 12 and the actual energy of the central atom (which is known from the generating step) is compared to the predicted <$y^1$>. If the predicted potential energy for a particular configuration is wrong by more than a prescribed amount, that configuration is added to the database at step 14. The process is continued until a stopping criterion is found to be met at step 15.

In some embodiments, the stopping criterion is whether the rate of adding new configurations has fallen below a threshold, for example that less than a threshold number of configurations out of every, for example, 1000 configurations produces an error big enough to be added to the database. A related stopping condition in some embodiments is that a certain number of configurations, for example 1000, 10000, 100000 or one million (or a value in between these values) has been generated and tested consecutively without any of them being added to the database. This is implemented, for example, by a counter which is reset to zero each time a configuration is added and stopping when the counter exceeds a threshold as described above.

In some embodiments, if an independent estimate is available for the property that is to be predicted (e.g. from a different physical model), the method can be used to store and later predict the difference between the crude estimate and the actual calculated value. In this way, the method can be used to improve an already existing model for predicting the property.

In some embodiments, the database is not generated by sequential error testing as described above, but rather a large set of N generated sample configurations is represented by much smaller number of M configurations such that a Gaussian Process using the M selected configurations has a minimised prediction error over all N samples of the large set. This corresponds to the standard machine learning problem of "sparsification", representing a large number of real-world collected data with a Gaussian Process over a limited number of data points (somewhat in analogy to a support vector machine).

First a large sample set (of size N) of atomic configurations and associated energies and forces is generated. This needs to encompass all kinds of configurations that the method will be used for (e.g. various solid phases, liquid, surfaces, etc.). The size of the database to be generated is determined, say M (with M<<N), and M pseudo-configurations are constructed in such a way that a Gaussian Process using the M pseudo data points will minimise the error of the prediction over all N Samples. The M configurations are designated as pseudo, because atomic configurations and target properties are not constructed for them explicitly, only the corresponding transformed coordinates, that is the bispectral invariants, are calculated. The construction can be achieved in $O(NM^2)$ steps and is hence linear in N. The construction has been described in detail in the Snelson and Ghahramani and the Quinonero-Candela and Rasmussen papers reference below and herewith incorporated by reference herein.

Estimating properties using a Gaussian Process on the resulting database takes only O(M) steps. In a particular embodiment for a single species materials model, N could be on the order of hundred thousand, and M could be a few hundred.

In some embodiments, the configurations are generated in a region of phase space where the energy is less than a threshold. For example, the configurations are generated at a temperature likely to be encountered in real materials, for example less than 5000° C.

The database can be fixed, or it can be extended on the fly, if a large error estimate is encountered for a particular configuration (see below), by calculating a new datapoint using the expensive quantum mechanical method that is being approximated. The new datapoint is then stored in the database for future use.

Parameter Estimation for New Configurations

Using the method is as follows, in overview. Incoming atomic configurations are compared using the covariance function to each of the database entries, and an estimate is made via the Gaussian Process for the potential energy and other derived quantities, e.g. the force on every atom, and the error in these estimates.

Figure 3:
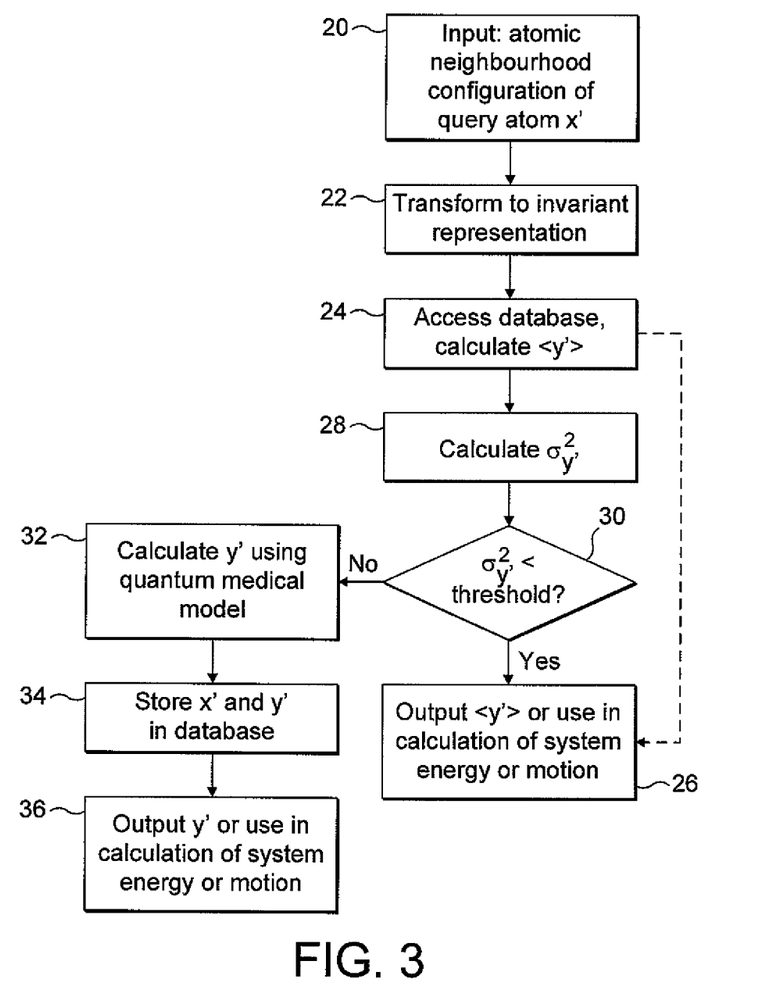
FIG. 3 shows a corresponding flow diagram describing the use of the embodiment.

With reference to FIG. 3, at step 20 a new atomic configuration x' is inputted to the system and is transformed to an invariant representation as described above at step 22. At step 24 the database is accessed and <y'> is calculated as an estimate of the property, such as energy of the central atom in the configuration, as described above. In some embodiments, the dashed arrow in FIG. 3 is then followed and at step 26 <y'> is output or passed to a further module for calculating the energy of a system of atoms or their motion for a system comprising a plurality of atomic neighbourhood configurations (this involves obtaining the property such as the energy, assumed to be local, for all neighbourhood configuration and combining them in a fashion well known to the person skilled in the art.

In alternative embodiments, the variance of the posterior distribution of y' is calculated at step 28. At step 30 a comparison is made between this variance and a threshold value which represents a limit on the acceptable variance (a measure of the confidence in the estimate) and if the variance is below the threshold, the method proceeds to step 26 described above.

If, however, the variance is equal or above the threshold, than an estimate (or exact solution) for y' is calculated using a (computationally expensive) quantum physics model at step 32 and the result is stored in the database together with x' at step 34 and output or used as in step 26 described above at step 36.

A further use of the method described above is the modeling of individual atomic energies. In quantum mechanical modelling the energy of individual atoms is not well defined, only the total energy of a collection of atoms can be calculated. Nevertheless, it is clear that a physically meaningful spatial partitioning of the total energy would be useful in understanding which atoms are "out-of-place", relatively speaking, in a particular configuration. A direct computational use would be, e.g. for the calculation of the formation energy of a surface, where the atoms close to the surface (the first few layers) "feel" the vacuum, but the atoms deeper in the bulk do not. Another use would be to aide the search for low energy configurations: this is typically done by optimizing the atomic positions, but the process get stuck in local minima, so some randomizing step is incorporated to try and nudge the system into ever lower local minima for each atom and towards the global energy minimum. Having a local energy quantity fear each atom would lead to a better optimization process because given a local minimum of the total energy, atoms with relatively high local energies should be randomized more.

In overview, this application involves a different way of calculating the database, which is specific for a given atomic configuration under study. The energy estimate for each atom based on its neighbourhood is then determined using a Gaussian Process, as described above.

Given an atomic configuration that is a local minimum of the total energy (as a result of known techniques for energy optimization) a trajectory is generated by uniformly expanding the spatial coordinates of the atoms step by step (e.g. by multiplying all coordinates by a factor at each step), and at the same time applying random displacements of various scales. At each step, the quantum mechanical total energy and forces are computed, until the atoms are so far away from each other that the forces are negligible. The resulting (typically few hundred) sets of atomic neighbourhood configurations (one for each step and one for each atom in the configuration under study) are used as the database in the method described above. Using the atomic neighbourhoods of the atoms in the original configuration as query atoms/configurations for the method described above, a local energy is calculated as the estimate produced at step 24 described above. For clusters and surfaces, this procedure produces local atomic energies that are intuitively meaningful chemically. The local energies can be used to visualize the original structure by colouring the atoms according to their local energies.

The database described above is only meaningful for a given original configuration, and needs to be regenerated for every starting structure. Databases generated this way result in "narrow but very accurate" models.

Alternatively, when aiding configuration optimization, this narrow database does not have to be generated by expanding the configuration as described above but the trajectory that led to the particular configuration during e.g. descent optimization can be used to provide the configurations for the database.

Many modifications and alterations of the embodiments described above by way of example only will occur to a person skilled in the art. All such modifications are intended to be covered by the scope of the appended claims.

In particular, the methods described above are not only applicable to estimating a property such as energy of a query atom, but can equally be used, in some embodiments, to estimate a property for a group of atoms (e.g. an amino acid) or a molecule in a corresponding configuration, e.g. a protein or a cell membrane, respectively. The idea of representing groups of atoms together is called "coarse graining" in the art of atomistic simulation. In this embodiment, then, the method is used to coarse grain an atomic scale model, which could be quantum mechanical or itself empirical.

The basic technology remains the same, apart from the source of the coordinates. A similar density function is used, with r and $r_i$ now corresponding to the centre of the groups or molecules in question and the length scale of the transformation enlarged. For the first transformation described above, this means more widely distributed and/or spaced basis functions $b_n$, as determined by the selection of the $r_n$ and $\sigma$. For the second transformation, this corresponds to a larger value of $r_0$ (see Appendix I).

If the orientation of the group or molecules is to be captured as well, this can be achieved in the same framework by replacing the single group/molecule centre r with two entries per group/molecule $r^+$ and $r^-$ spaced apart to define a dipole, as is well known in the art of molecular simulations.

In an alternative embodiment, instead of recording potential energies of atoms in the database, one can record neighbourhoods or environments of pairs of atoms, i.e. atomic bonds. This is an equivalent representation of the configuration of an atomic system. The environment of the bond is in turn characterised by the environments of the two atoms that comprise it. This is a larger space of possibilities, and will lead to a more accurate approximation of the quantum mechanical potential energy.

Furthermore, in materials where the atoms are significantly charged (ionic crystals, ceramics, biologically relevant substances), the potential energy of an atom is not purely local: not a function of its immediate neighbourhood only, but depends on the local electrostatic field, which itself is a function of the positions and charges of all atoms in the system. Established empirical interatomic potentials treat this problem by defining (and usually fixing) the polarizability and/or the chemical hardness of an atom (the ease with which it changes its charge state), from which a self-consistent solution of the local electric field and thus the potential energy can be obtained. For these materials, the method is modified as follows. One database is created to describe the component of the potential energy that is local. A second database is built, using the same principles, to approximate the polarizability as a function of the neighbourhood. The modification to the method is minimal, since the description of the neighbourhoods in both databases is identical. The two databases are then combined to approximate the potential energy.

Another alternative is that instead of using data on energies of atoms, one can recast the above Gaussian Process to do the inference from forces on atoms (which are just the derivatives of the total energy with respect to the atomic positions). The predicted quantity would still be the local part of the energy, polarizability, chemical hardness, etc. Such a recasting is explained in the doctoral thesis by S. Ahnert (Cambridge University), incorporated herewith by referenced herein.

It will be understood that where the above description refers to method and algorithm step, this reference includes a reference to the execution of the steps in software and/or hardware, for example on a general purpose computer system.

References

The following references are herewith incorporated by reference herein:

Ahnert, Sebastian E, PhD Thesis, University of Cambridge, 2005

Imre Risi Kondor, "A novel set of rotationally and translationally invariant features for images based on the non-commutative bispectrum", arxiv:cs/0701127v3 (2007)

MacKay, David J C, "Information Theory, Inference, and Learning Algorithms", Cambridge University Press, 2003

Rasmussen, Carl and Williams, Christopher, K I, "Gaussian Processes for Machine Learning", MIT Press, 2006

Skilling, J, "Nested Sampling for General Bayesian Computation", International Society for Bayesian Analysis, 2006

Snelson, Edward; Ghahramani, Zoubin: "Sparse Gaussian processes using pseudo-inputs" in Advances in neural information processing systems 18, MIT Press; 2006; Weiss, Y.; Schölkopf, B.; Platt, J.; (editors) Pages 1257-1264

"A Unifying View of Sparse Approximate Gaussian Process Regression"; Joaquin Quinonero-Candela, Carl Edward Rasmussen, Journal of Machine Learning Research 6 (2005); 1939-1959

D A Varshalovich, A N Moskalev, V K Khersonskii: "Quantum Theory of Angular Momentum", Singapore, Teaneck, N.J., USA World Scientific Pub 1988

Multiple expansions in four-dimensional hyperspherical harmonics," a V Meremianin, J. Phys. A: Math. Gen. 39 (2006), 3099-3112.

APPENDIX I

We project a function in 3 dimensional space onto the 4 dimensional sphere. Each coordinate becomes $$(x,y,z) \rightarrow (\phi, \theta, \theta_0) \quad (1)$$

A possible way of projecting a three-dimensional object onto the surface of the four-dimensional sphere is described as follows. Only points that $\sqrt{x^2+y^2+z^2} < r_{cut} < r_0 * \pi$ are considered in this approach.

$$\phi = \arctan \frac{y}{x}$$

$$\theta = \arccos \frac{z}{\sqrt{x^2+y^2+z^2}}$$

$$\theta_0 = \frac{\sqrt{x^2+y^2+z^2}}{r_0}.$$

The spherical harmonics of the 4 dimensional sphere are the three dimensional finite rotation matrices, as $U_l^{m'm}(2\theta_0, \theta, \phi)$. (If these are represented in terms of Euler angles, they are called "Wigner-matrices" or "Wigner-functions", but in this case, they are represented in terms of an axis—given by the two polar angles—and the angle of rotation around this axis.

Therefore the Fourier-coefficients of the points on the sphere are $$c_l^{m'm} = \langle U_l^{m'm} | f \rangle. \quad (2)$$

A cutoff function is also applied, ensuring smooth transition at the cutoff radius:

$$f_c(r) = \begin{cases} 0 & r > r_{cut} \\ \frac{1}{2}\cos\left(\frac{\pi r}{r_{cut}}\right) + \frac{1}{2} & r \leq r_{cut} \end{cases} \quad (3)$$

The following expansion formula holds for the product of two hyperspherical harmonics:

$$U_{l_1}^{m'_1 m_1} U_{l_2}^{m'_2 m_2} = \sum_{l=|l_1-l_2|}^{l_1+l_2} C_{l,l_1,l_2}^{m,m_1,m_2} C_{l,l_1,l_2}^{m',m'_1,m'_2} U_l^{m'm} \quad (4)$$

where $C_{l,l_1,l_2}^{m,m_1,m_2}$ are the ordinary Clebsch-Gordan coefficients.

I define the bispectrum as $$p_{l_1,l_2,l} = \sum_{m'_1,m_1=-l_1}^{l_1} \sum_{m'_2,m_2=-l_2}^{l_2} \sum_{m',m=-l,l}^{l} (c_l^{m'm})^* C_{l,l_1,l_2}^{m,m_1,m_2} C_{l,l_1,l_2}^{m',m'_1,m'_2} c_{l_1}^{m'_1 m_1} c_{l_2}^{m'_2 m_2} \quad (5)$$

which simplifies because all Clebsch-Gordan coefficients $m \neq m_1 + m_2$ are 0:

$$p_{l_1,l_2,l} = \sum_{m'_1,m_1=-l_1}^{l_1} \sum_{m',m=-l}^{l} (c_l^{m'm})^* C_{l,l_1,l_2}^{m,m_1,m-m_1} C_{l,l_1,l_2}^{m',m'_1,m'-m'_1} c_{l_1}^{m'_1 m_1} c_{l_2}^{m'-m'_1,m-m_1} \quad (6)$$

APPENDIX II

In the sparsification procedure, we take a very large dataset of size N which is supposed to cover all kinds of configurations that we are ever likely to encounter. N can be a million or more. We wish to represent this data with samples at just M points, M<<N, in such a way that the error based on our smaller representation as measured using the large dataset is as small as possible. We use a Sparse Gaussian Process for this.

Teaching Points:
$x_n$: nth teaching point in the large set (given)
$\bar{x}_m$: mth sparse teaching point (to be found)
$x_*$: query point
Covariance Matrices:

$$[C_M]_{mm'} = C(\bar{x}_m, \bar{x}_{m'})$$

$$[C_{NM}]_{nm} = [k_n]_m = C(x_n, \bar{x}_m)$$

$$[k_*]_m = C(\bar{x}_m, x_*)$$

$$[\lambda]_n = C(x_n, x_n) - k_n^T C_M^{-1} k_n$$

$$\Lambda = \text{diag}(\lambda)$$

The covariance of the M points in the sparse set:

$$Q_M = C_M + C_{MN}(\Lambda + \sigma^2 I)^{-1} C_{NM}$$

Our estimate at $x_*$:

$$\mu_* = k_*^T Q_M^{-1} C_{MN} (\Lambda + \sigma^2 I)^{-1} y$$

And the error:

$$\sigma_*^2 = C(x_*, x_*) - k_*^T (C_M^{-1} - Q_M^{-1}) k_* + \sigma^2$$

Notice that to use our small database, only needs to be computed, which is an O(M) operation. The preparation of the small database is $O(N M^2)$, i.e. linear in N.

In order to generate the optimal database, we maximise the following likelihood function with respect to every parameter in covariance function and $\bar{x}_m$, $$\log L = -\frac{1}{2} y^T (C_{NM} C_M^{-1} C_{MN} + \Lambda + \sigma^2 I)^{-1} y - \frac{1}{2} \log |C_{NM} C_M^{-1} C_{MN} + \Lambda + \sigma^2 I| - \frac{n}{2} \log 2\pi$$

The invention claimed is:

1. A method of estimating a property for a query object in a corresponding query object configuration, the method comprising:
   accessing a database of database object configurations and a corresponding value of a property for each respective database object in each database configuration, wherein the query object configuration is different from any of the database object configurations;
   calculating an estimate of a query value of the property for the query object in the query object configuration as a mean of a posterior distribution over the query value for the query object under a Gaussian Process model, wherein the objects are atoms, groups of atoms or molecules; and
   providing the estimate in an answer to a query;
   wherein:
   (a) the database object configurations are stored in the database as a list of object coordinates relative to a respective object and calculating the estimate includes transforming the relative object coordinates into a representation which is invariant under rotation and permutation, or
   (b) the method includes transforming relative object coordinates of object configurations into a representation which is invariant under rotation and permutation and storing the transformed object configurations in the database as the database object configurations;
   wherein the transforming in (a) and (b) comprises:
   (c) transforming the relative object coordinates into a basis comprising a product of spherical harmonics and radial basis functions and calculating selected values of the bi-spectrum from the transformed coordinates, or
   (d) projecting the relative object coordinates onto a 4-dimensional sphere, calculating spherical harmonics of the projected coordinates, and calculating selected values of the bi-spectrum from the spherical harmonics of the projected coordinates.

2. A method as claimed in claim 1, wherein the relative object coordinates are relative Cartesian object coordinates; and wherein the transforming includes projecting the relative Cartesian object coordinates onto a 4-dimensional sphere and then calculating the spherical harmonics of the projected coordinates.

3. A method as claimed in claim 1, wherein the property is energy.

4. A method as claimed in claim 3, further comprising estimating the local contribution of a query atom to the energy of the atoms of a physical object by estimating the local contribution as the energy of the query atom using the preceding steps.

5. A method as claimed in claim 4, further comprising changing a study configuration stepwise and at each step recording the neighbourhood configurations of all atoms in the study configuration in the database as database configurations.

6. A method as claimed in claim 1, wherein the property estimated by the method is different from the property stored in the database.

7. A method as claimed in claim 6, wherein the property stored in the database is the force, and the property estimated is the energy.

8. A method as claimed in claim 1, wherein the query object and the database objects are at the centre of their respective configuration.

9. A method as claimed in claim 1, further comprising estimating a measure representative of the variance of the posterior distribution and, if the measure exceeds a threshold, calculating the query value using a quantum mechanical model and adding the query atomic configuration and so calculated query value to the database.

10. A method as claimed in claim 1, further comprising estimating the energy of atoms of a physical object comprising a plurality of atomic configurations by estimating a value of a property for each atom of the atomic configurations based on the preceding steps and calculating an estimate of the energy using the estimated values.

11. A method as claimed in claim 1, further comprising estimating the motion of atoms of a physical object comprising a plurality of atomic configurations by estimating a value of a property for each atom of the atomic configurations by the preceding steps and calculating an estimate of the motion using the estimated values.

12. A method as claimed in claim 1, further comprising building the database by generating a new neighbourhood configuration not in the database for which a corresponding new value of the property is known, calculating an estimated value of the property by the preceding steps, calculating an estimation error by comparing the new value and the estimated value and adding the new configuration and value to the database if the error exceeds a threshold.

13. A method as claimed in claim 12, further comprising repeating the steps until a rate of adding new configurations to the database drops below a threshold.

14. A method as claimed in claim 12, further comprising repeating the steps until a predetermined number of consecutive new configurations has been detected not to have been added to the database.

15. A method as claimed in claim 1, further comprising generating a first number of configurations of objects, calculating a corresponding property value for each of the first number of configurations and defining a second number of database entries to define the database, wherein the first number is larger than the second number and the database entries are defined such that an error between the calculated property value and a value of the property estimated based on the database is minimised for the generated configurations.

16. A method as claimed in claim 1, wherein the relative object coordinates are relative Cartesian object coordinates.

17. A method as claimed in claim 1, wherein the transforming includes projecting the relative object coordinates onto a 4-dimensional sphere and then calculating the spherical harmonics of the projected coordinates.

18. A method as claimed in claim 1, wherein the transforming includes transforming the relative object coordinates into a basis comprising a product of spherical harmonics and radial basis functions and calculating selected values of the bi-spectrum from the transformed coordinates.

19. One or more non-transitory computer-readable media storing instructions which, when executed by one or more processors, cause performance of a method of estimating a property for a query object in a corresponding query object configuration, the method comprising:
   accessing a database of database object configurations and a corresponding value of a property for each respective database object in each database configuration, wherein the query object configuration is different from any of the database object configurations;
   calculating an estimate of a query value of the property for the query object in the query object configuration as a mean of a posterior distribution over the query value for the query object under a Gaussian Process model, wherein the objects are atoms, groups of atoms or molecules; and
   providing the estimate in an answer to a query;
   wherein:
      (a) the database object configurations are stored in the database as a list of object coordinates relative to a respective object and calculating the estimate includes transforming the relative object coordinates into a representation which is invariant under rotation and permutation, or
      (b) the method includes transforming relative object coordinates of object configurations into a representation which is invariant under rotation and permutation and storing the transformed object configurations in the database as the database object configurations;
   wherein the transforming in (a) and (b) comprises:
      (c) transforming the relative object coordinates into a basis comprising a product of spherical harmonics and radial basis functions and calculating selected values of the bi-spectrum from the transformed coordinates, or
      (d) projecting the relative object coordinates onto a 4-dimensional sphere, calculating spherical harmonics of the projected coordinates, and calculating selected values of the bi-spectrum from the spherical harmonics of the projected coordinates.

20. One or more non-transitory computer-readable media as claimed in claim 19, wherein the relative object coordinates are relative Cartesian object coordinates.

21. One or more non-transitory computer-readable media as claimed in claim 19, wherein the property is energy.

22. One or more non-transitory computer-readable media as claimed in claim 19, wherein the transforming includes projecting the relative object coordinates onto a 4-dimensional sphere and then calculating the spherical harmonics of the projected coordinates.

23. One or more non-transitory computer-readable media as claimed in claim 19, wherein the transforming includes transforming the relative object coordinates into a basis comprising a product of spherical harmonics and radial basis functions and calculating selected values of the bi-spectrum from the transformed coordinates.

* * * * *

UNITED STATES PATENT AND TRADEMARK OFFICE
CERTIFICATE OF CORRECTION

PATENT NO. : 8,843,509 B2  Page 1 of 1
APPLICATION NO. : 12/996530
DATED : September 23, 2014
INVENTOR(S) : Gabor Csanyi et al.

It is certified that error appears in the above-identified patent and that said Letters Patent is hereby corrected as shown below:

In the Claims

COLUMN 14

Claim 19: Line 10: Delete "method-of" and insert --method of--.

Signed and Sealed this
Second Day of December, 2014

Michelle K. Lee
*Deputy Director of the United States Patent and Trademark Office*